United States Patent
Nowak et al.

(10) Patent No.: US 6,867,246 B2
(45) Date of Patent: Mar. 15, 2005

(54) N-ALKYL AZIRIDINE BLOCK COPOLYMERS AND THE USES THEREOF

(75) Inventors: Reinhold Nowak, Adelshofen (DE); Joachim Zech, Kaufering (DE); Peter Bissinger, Diessen (DE); Erich Wanek, Kaufering (DE); Gunther Eckhardt, Frieding (DE); Guenther Lechner, Woerthsee (DE)

(73) Assignee: 3M Espe AG, Seefeld (DE)

(*) Notice: Subject to any disclaimer, the term of this patent is extended or adjusted under 35 U.S.C. 154(b) by 0 days.

(21) Appl. No.: 10/296,996

(22) PCT Filed: May 30, 2001

(86) PCT No.: PCT/EP01/06141

§ 371 (c)(1),
(2), (4) Date: Jul. 8, 2003

(87) PCT Pub. No.: WO01/92374

PCT Pub. Date: Dec. 6, 2001

(65) Prior Publication Data

US 2004/0014907 A1 Jan. 22, 2004

(30) Foreign Application Priority Data

May 31, 2000 (DE) ........................................ 100 26 852

(51) Int. Cl.$^7$ ................................................ A61K 6/10
(52) U.S. Cl. ........................ 523/109; 523/107; 523/115; 528/27; 528/28
(58) Field of Search ..................... 528/27, 28; 525/474; 523/107, 109, 115

(56) References Cited

U.S. PATENT DOCUMENTS

| | | | |
|---|---|---|---|
| 3,159,600 A | | 12/1964 | Watkins et al. |
| 3,243,429 A | * | 3/1966 | Ham ........................... 548/955 |
| 3,453,242 A | | 7/1969 | Schmitt et al. |
| 4,093,555 A | | 6/1978 | Schmitt et al. |
| 4,167,618 A | | 9/1979 | Schmitt et al. |
| 5,569,691 A | | 10/1996 | Guggenberger et al. |
| 2004/0014924 A1 | * | 1/2004 | Nowak et al. ................ 528/28 |

FOREIGN PATENT DOCUMENTS

| | | |
|---|---|---|
| DE | 914325 | 7/1954 |
| DE | 3741575 | 6/1988 |
| DE | 3838587 | 5/1990 |
| DE | 4010281 | 10/1990 |
| DE | 4019249 | 8/1991 |
| DE | 4306997 | 9/1994 |
| DE | 19719438 | 11/1997 |
| DE | 19942459 | 3/2001 |
| DE | 10018918 | 11/2001 |
| EP | 0110429 | 12/1983 |
| EP | 0982041 | 8/1999 |
| JP | 60094486 | 5/1995 |
| WO | 00/47165 | 8/2000 |

* cited by examiner

*Primary Examiner*—Margaret G. Moore
*Assistant Examiner*—Marc S Zimmer
(74) *Attorney, Agent, or Firm*—Crowell & Moring LLP

(57) ABSTRACT

N-alkyl aziridine block copolymers of the general structure (1), wherein R1 represents H, $C_1$–$C_{12}$ alkyl, $C_2$–$C_{12}$ alkenyl, $C_2$–$C_{12}$ alkinyl, $C_7$–$C_{15}$ aralkyl $C_7$–$C_{15}$ aralkyl, or $C_3$–$C_{12}$ cycloalkyl and these groups can be substituted with Cl or F partially, completely or in a mixed manner and/or may contain 0 to 5 heteroatoms selected from O, N, S; R2 represents a group selected from R1 and/or R4; R3 represents $SiR1_3$ or $SiR1_2R4$, wherein R4 represents a group of the general formula (2), wherein A represents an (n+1) radical saturated, unsaturated or aromatic, linear, branched or cyclic hydrocarbon group that may contain 0 to 5 heteroatoms selected from O, N, S and that comprises 1 to 18 carbon atoms; B is selected from O, S, NR1; D is selected from C(O)O, C(O)NR1, C(O), C(S)NR1, $CH_2$; E represents a diradical saturated or unsaturated, linear, branched or cyclic hydrocarbon group that may contain 0 to 5 heteroatoms selected from O, N, S, and that comprises 0 to 18 carbon atoms; Q represents and α, ω-radical polyether chain of the general formula (3): —[O—$C_gH_{2g}$]$_h$—, wherein g is 2 to 20; h is 1 to 1000; a is 0 or 1; f is an integer from 2 to 1000; n is an integer from 1 to 10; and x, y, z each represents 0 or an integer, the sum of which should range between 1 and 10000, with the proviso that if x is larger 0, y or z is smaller or equal x. There are many uses of these copolymers.

18 Claims, No Drawings

N-ALKYL AZIRIDINE BLOCK COPOLYMERS AND THE USES THEREOF

The invention relates to N-alkylaziridine block copolymers and the use thereof, in particular in dental preparations.

In the context of this invention, N-alkylaziridine block copolymers are understood as meaning oily or resin-like polymers which have a silicone core block which is linked to a plurality of polyether blocks, to the respective other end of which in turn aziridino groups are linked.

High-precision elastic impression materials which are distinguished by high molding accuracy, high dimensional stability and good detail reproduction are, for example, materials based on agar agar, polysulfides, polyethers or addition-crosslinking silicones.

In the case of the addition-crosslinking silicone impression materials, the curing is achieved by reaction of a polysiloxane having terminal vinyl groups with a polysiloxane having Si—H groups by means of platinum catalysts. The impressions thus obtained are distinguished by very good elastic properties and long shelf lives. The disadvantage of these materials has always been the low hydrophilicity, which leads to insufficient reproduction of detail because of a poor flowability.

In order to improve the hydrophilic behavior of silicone impression materials, hydrophilizing additives are added to the addition-crosslinking silicone impression materials. However, the better wettability thus achieved is also associated with increased water absorption on contact with moist media, which can result in poorer dimensional stability and increased hydrogen evolution.

In the case of the pure polyether materials, aziridine-containing substances are polymerized, as described in U.S. Pat. Nos. 3,453,242 and 4,093,555 or in DE-A-43 06 997. For example, the sulfonium salts disclosed in U.S. Pat. No. 4,167,618 are suitable for initiating the polymerization. The polyether impression materials thus prepared have natural hydrophilic properties.

There were various approaches for combining the hydrophilic properties of the polyether with the good elastic properties of the silicones:

DE-A-3 741 575, DE-A-40 19 249, DE-A-40 10 281 and DE-A-38 385 87 describe materials based on a platinum-catalyzed addition reaction of an Si—H component with an unsaturated polyether. In contrast to addition-crosslinking silicones, the unsaturated polyether is, as a rule, the main component which imparts the hydrophilic character to the matrix.

DE-A-40 19 249 describes curable materials which, in addition to unsaturated polyethers having terminal alkenyl radicals, also contain the reaction products of substituted polyethers with oligosiloxanes having at least two Si—H groups in the molecule and platinum catalysts as main components.

In order to obtain a sufficient shelf-life, it is necessary spatially to separate the reactive components from one another. Here, the Si—H compounds and the platinum catalysts required for curing at room temperature cannot be combined to provide a paste, since decomposition of the Si—H compound occurs.

In the course of storage over a period of several weeks and months, however, the problem arises that a catalyst component in which the platinum catalyst is present together with the unsaturated polyether also has an unsatisfactory shelf life.

For the dentist or the technician, however, it is necessary to have available an impression material which has a long shelf life and whose usability is guaranteed over a period of several months to years.

DE-A-40 10 281 therefore proposes the addition of antioxidants for increasing the shelf life. However, this too results only in unsatisfactory long-term storage stability.

DE-A-197 19 438 describes addition-crosslinking polyether impression materials which are distinguished by a good shelf life of the catalyst component and of the base component as well as of the cured dental material. The disadvantage of these dental materials is the low level of the mechanical properties, so that they can be used only to a limited extent for taking dental impressions.

It is an object of the present invention to provide materials which do not have the disadvantages of the prior art.

This object was achieved by N-alkylaziridine block copolymers as a basis for the preparation of curable materials which are described in the claims.

The individual components of the materials prepared therefrom have a good shelf life. For example, when used as dental materials, a high molding accuracy is achieved. In the cured state, they are distinguished by good mechanical properties.

The N-alkylaziridine block copolymers used according to the invention have the general structures shown below, according to the formula (1):

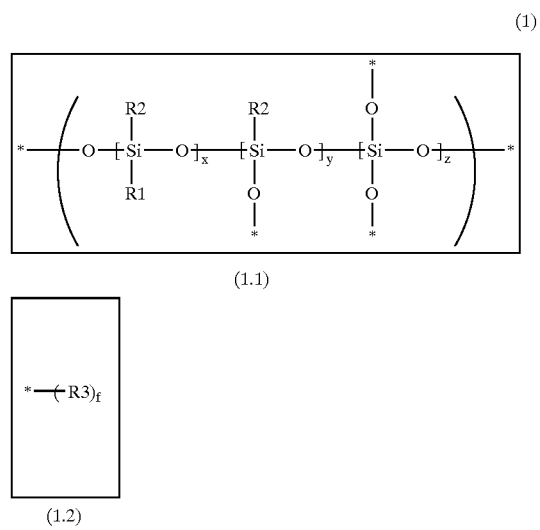

in which

R1 denotes H, $C_1$–$C_{12}$-alkyl, $C_2$–$C_{12}$-alkenyl, $C_2$–$C_{12}$-alkynyl, $C_7$–$C_{15}$-alkaryl, $C_7$–$C_{15}$-aralkyl or $C_3$–$C_{12}$-cycloalkyl and these radicals may be partly or completely substituted by Cl or F or a mixture thereof and/or may contain 0 to 5 hetero atoms from the group consisting of O, N and S; H, methyl, ethyl, ethenyl, propenyl, phenyl, tolyl, 2-ethylphenyl and cyclohexenyl are preferred;

R2 denotes a radical from the group R1 and/or R4;

R3 denotes $SiR1_3$ or $SiR1_2R4$ with:

R4=a representative of the general formula (2):

$$*-A-(Q-[B]_a-D-E-N\overset{R1}{\underset{}{\triangleleft}})_n \quad (2)$$

in which:
   A=a (n+1)-valent saturated, unsaturated or aromatic, linear, branched or cyclic hydrocarbon radical which may contain 0 to 5 hetero atoms from the group consisting of O, N and S and comprises 1 to 18 carbon atoms, preferably 1 to 12 carbon atoms;
   B=a representative of the group O, S, NR1;
   D=a representative of the group C(O)O, C(O)NR1, C(O), C(S)NR1 and $CH_2$;
   E=a divalent saturated or unsaturated, linear, branched or cyclic hydrocarbon radical which may contain 0 to 5 hetero atoms from the group consisting of O, N and S and comprises 0 to 18 carbon atoms, preferably 1 to 12 carbon atoms;
   Q=an α,ω-polyether chain of the general formula (3):

$$-[O-C_gH_{2g}]_h- \quad (3)$$

in which
   g denotes 2 to 20, preferably 2 to 10, particularly preferably 2 to 7;
   h denotes 1 to 1000, preferably 1 to 500, particularly preferably 1 to 200;
   a denotes 0 or 1;
   f denotes an integer from 2 to 1000, preferably 2 to 100, particularly preferably 2 to 50;
   n denotes an integer from 1 to 10, preferably 1 to 5, particularly preferably 1 to 3;
and
x, y and z each represent either 0 or integers whose sum should be between 1 and 10 000, preferably between 1 and 1 000 and particularly preferably between 10 and 500, it being possible for the average molar mass $M_n$ of the products to be preferably between 500 and 50 000 and particularly preferably between 1 000 and 20 000,
   with the limitations that, if x is greater than 0, y or z should be less than or equal to x, preferably less than or equal to 0.05 times x and particularly preferably 0.02 times x.
   The symbol "*" in the formula (1.2) means that the valency thus marked is linked to those positions of the fragment (1.1) which are marked "*".
   Of the respective x radicals of R2, up to 0.5 times x may denote radicals R4 and the others denote R1.
   Linear polysiloxanes are present in the case of y+z=0, and branched polysiloxanes in the case of y+z>0, it being necessary to understand the formula (1) in such a way that, in this case, the polymer can contain both D and T and/or Q units in the meaning of silicone nomenclature, which may be in any desired position in the molecule and, at the linkage points of the T and Q units, have D chains of any desired length, the total length of which is xD units.
   Each mention of the radical R1 merely means that it is taken from the selection made under R1, and different mentions can mean different radicals R1 at each different substitution point and also on each repeating unit of a polymeric formula. In other words, the factor $-(SiOR1R2)_x-$ means both homopolymers having a defined R1 and R2 and copolymers of silicones of different radicals R1 and R2, but x denotes the number of all silicone atoms included thereby, without inclusion of the selection of radicals R1 and R2 made. An analogous situation also applies in context for the factor $-(SiR2(O*))_y-$ and R3.

In general, no uniform parent polysiloxane chains are present. Depending on the preparation process, the polydispersity ($M_w/M_n$) may be 1.1 to 20 and preferably 1.2 to 10.

Depending on the preparation process, the polydispersity of the polyether blocks may be 1.1 to 20 and preferably 2 to 10.

The polyether block may be a homopolymer, a copolymer or a terpolymer. The copolymers may have an alternate or random composition or have alternate and random copolyether blocks which are optionally linked to homopolymeric polyether blocks.

Preferred polyether blocks are polytetrahydrofuran, polypropylene oxide, random copolymers of ethylene oxide and tetrahydrofuran, of propylene oxide and tetrahydrofuran and of ethylene oxide and propylene oxide, block copolymers of ethylene oxide and propylene oxide and random terpolymers of ethylene oxide, propylene oxide and tetrahydrofuran.

Preferred representatives of the formula (2) are the following, the N-alkylpropyleneimine derivatives being meant in addition to the N-alkylethyleneimine derivatives:

from: $A=(CH_2)_z$; B=O; D=C(O)NR1 (with R1=H); E=1,3-propanediyl; a=1; n=1 from: $A=(CH_2)_z$; B=NH; D=C(O)NR1 (with R1=H); E=1,3-propanediyl; a=1; n=1 from: $A=(CH_2)_z$; B=O; D=C(O)NR1 (with R1=H); E=2-methyl-1,3-propanediyl; a=1; n=1 from: $A=(CH_2)_z$; B=NH; D=C(O)NR1 (with R1=H); E=2-methyl-1,3-propanediyl; a=1; n=1

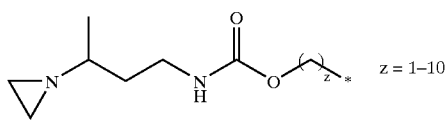

from: A=(CH$_2$)$_z$; B=O; D=C(O)NR1 (with R1=H); E=1,3-butanediyl; a=1; n=1

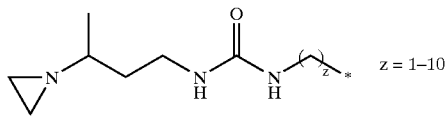

from: A=(CH$_2$)$_z$; B=NR1 (R1=H); D=C(O)NR1 (with R1=H); E=1,3-butanediyl; a=1; n=1

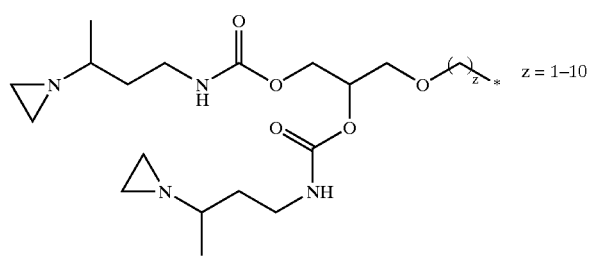

from: A=3-oxaheptane-1,2,7-triyl (for z=3); B=O; D=C(O)NR1 (with R1=H); E=1,3-butanediyl; a=1; n=2

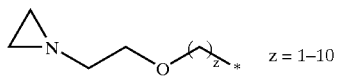

from: A=(CH$_2$)$_z$; B=O; D=CH$_2$; E=methanediyl; a=1; n=1

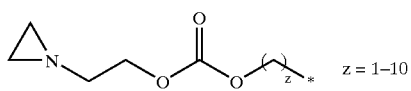

from: A=(CH$_2$)$_z$; B=O; D=C(O)O; E=1,2-ethanediyl; a=1; n=1

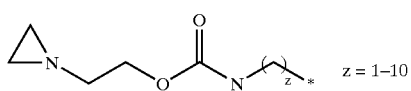

from: A=(CH$_2$)$_z$; B=O; D=C(O)O; E=1,2-ethanediyl; a=1; n=1

from: A=(CH$_2$)$_z$; D=CH$_2$; E=CH$_2$; a=0; n=1

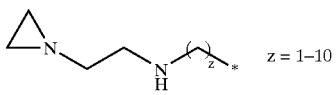

from: A=(CH$_2$)$_z$; B=NH; D=CH$_2$; E=1,2-ethanediyl; a=1; n=1

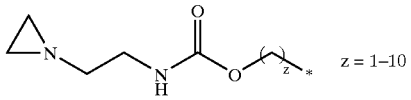

from: A=(CH$_2$)$_z$; B=NH; D=C(O)O; E=1,2-ethanediyl; a=1; n=1

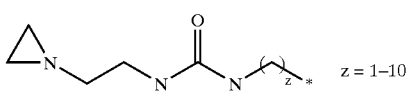

from: A=(CH$_2$)$_z$; B=NH; D=C(O)NH; E=1,2-ethanediyl; a=1; n=1

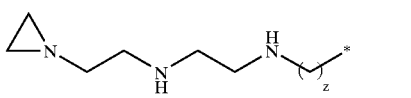

from: A=(CH$_2$)$_z$; B=NH; D=CH$_2$; E=2-aza-1,4-butanediyl; a=1; n=1

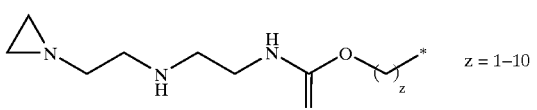

from: A=(CH$_2$)$_z$; B=NH; D=C(O)O; E=2-aza-1,4-butanediyl; a=1; n=1

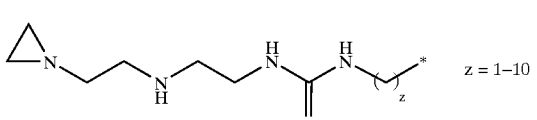

from: A=(CH$_2$)$_z$; B=NH; D=C(O)NH; E=2-aza-1,4-butanediyl; a=1; n=1

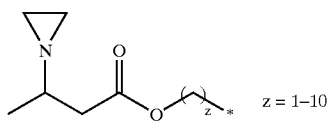

from: A=(CH$_2$)$_z$; B=O; D=C(O); E=2-methyl-1,2-propanediyl; a=1; n=1

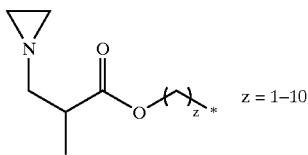

from: A=(CH$_2$)$_z$; B=O; D=C(O); E=1-methyl-1,2-propanediyl; a=1; n=1

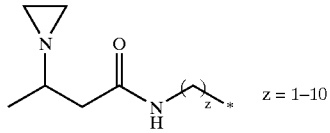

from: A=(CH$_2$)$_z$; B=NH; D=C(O); E=2-methyl-1,2-propanediyl; a=1; n=1

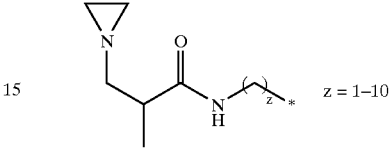

from: A=(CH$_2$)$_z$; B=NH; D=C(O); E=1-methyl-1,2-propanediyl; a=1; n=1

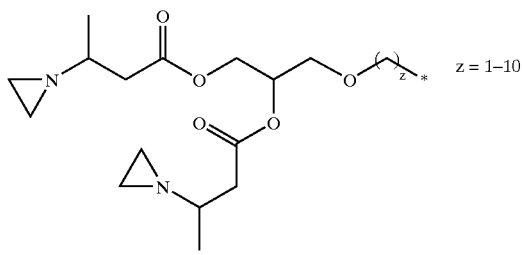

from: A=3-oxaheptane-1,2,7-triyl; B=O; D=C(O); E=2-methyl-1,2-propanediyl; a=1; n=2

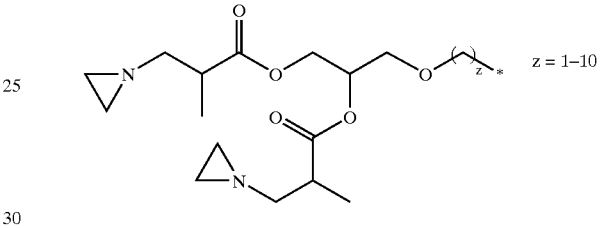

from: A=3-oxaheptane-1,2,7-triyl; B=O; D=C(O); E=1-methyl-1,2-propanediyl; a=1; n=2

The N-alkylaziridine block copolymers according to the invention may have molar masses in the range from 500 to 50 000 g/mol, preferably from 1 000 to 30 000 g/mol and particularly preferably in the range from 3 000 to 20 000 g/mol. They have at least one and preferably up to ten N-alkylaziridino groups in the molecule. The use of mixtures of N-alkylaziridine block copolymers and different molar masses and different numbers of N-alkylaziridino groups is possible and is used for establishing the properties of materials formulated therefrom.

For establishing the respective desired network structure, the N-alkylaziridine block copolymers according to the invention may have very different aziridino equivalent masses, the range from 250 to 25 000 g/equivalent and in particular from 400 to 10 000 g/equivalent being preferred.

In principle, in the preparation of N-alkylaziridine block copolymers according to the invention, a commercially available functionalized polysiloxane is converted in one or more steps into the aziridine block copolymer. Instead of using the commercially available functionalized polysiloxanes as such, a mixture of these and/or a mixture of these with silicone raw materials can also be modified by equilibration, polymerization, copolymerization, depolymerization, etc. in a known manner (cf. P. Kochs in Houben-Weyl, Vol. E20, page 2219 et seq.) and only thereafter functionalized to give the aziridine block copolymer. A large number of preferred representatives of such functionalized silicone oils can be found, for example, in the catalog "Reactive Silicones" of the company Gelest. However, they can even be prepared according to methods known from the literature, for example according to H. R. Kricheldorf (Ed.), "Silicon in Polymer Synthesis", Springer 1996, Chapter 3. Hydrido-, hydroxyalkyl- and aminoalkyl-functionalized siloxanes are particularly suitable for the functionalization.

Such functionalized silicones can then be converted into the polyether-silicone block copolymers according to the

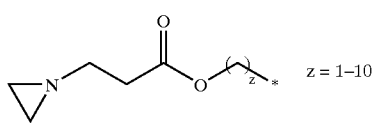

from: A=(CH$_2$)$_z$; B=O; D=C(O); E=1,2-ethanediyl; a=1; n=1

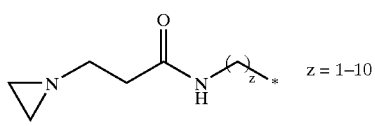

from: A=(CH$_2$)$_z$; B=NH; D=C(O); E=1,2-ethanediyl; a=1; n=1

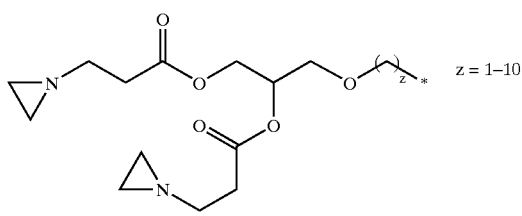

from: A=3-oxaheptane-1,2,7-triyl; B=O; D=C(O); E=1,2-ethanediyl; a=1; n=2 invention in various ways. For stability reasons, block copolymers in which links via hydrolytically unstable Si—O—C bonds are avoided in favor of hydrolytically stable Si—C bonds are preferred. On the other hand, block copolymers having Si—O—C bonds are preferred for cost reasons, since in this case the very economical silanol-terminated silicone oils can be used as starting materials. The linkage of polyether blocks can be effected, for example, by cationic graft polymerization of cyclic ethers or mixtures thereof on silicone structures having protic terminal groups. Another possibility is the linkage of chloroformates, chlorooxalates and other monoester/monoamide chlorides of such silicone structures with polyetherdiols. A further possibility is the hydrosilylation of polyether monoallyl ethers of hydrido-functionalized silicone oils. By hydrosilylation of silicone monomers, such as $M^H{}_2$ or $D^H{}_m$ (according to conventional silicone nomenclature: Encyclopedia of Polymer Science and Engineering, 2nd Ed., Vol. 15, page 206 et seq.; H=hydrido-functionalized) and subsequent equilibration with a silicone structure or copolymerization, for example with $D_4$, the object can likewise be achieved. These and further silicone-polyether block copolymers can be prepared by methods in J. B. Plumb et al., "Block Copolymers", Applied Science Pub., 1973, page 306 et seq.

Aziridine compounds can be prepared from the block copolymers, for example via chlorooxalates or chloroformates, in some cases activated amides, such as imidazolides, being prepared as intermediates from the chlorooxalates or chloroformates. Suitable aziridine components are, for example, aziridinoethanol (Acros) or other hydroxyl- or amino-functional aziridine compounds.

In addition to these methods for synthesizing aziridine compounds, a large number of possible synthesis variants for the synthesis and for the derivatization or modification of aziridine compounds appear in the following monographs and in the literature cited therein. The preferred representatives of the aziridinosilicones and, if required, their precursors can be prepared by the procedures described there, it being necessary for a person skilled in the art to adapt some of these methods for the present context: R. C. Elderfield, "Heterocyclic Compounds", Vol. 1, pages 61–77, Wiley 1950; Houben-Weyl "Methoden der Organischen Chemie" [Methods of organic chemistry], Vol. XI/2, page 223–264, Thieme 1958; O. C. Dermer, G. E. Ham, "Ethyleneimine and other Aziridines", in particular pages 106–205 and pages 340–393, Academic Press 1969; Houben-Weyl "Methoden der Organischen Chemie" [Methods of organic chemistry], Vol. E16c, pages 370–667, Thieme 1992; Ulmanns Encyclopedia of Industrial Chemistry 5th Ed., Vol. A3, pages 239–243.

The invention furthermore relates to curable materials based on the N-alkylaziridine block copolymers according to the invention, in particular two component dental material, these containing the following, based in each case on 100 parts by mass, after mixing of the components:
(A) 30 to 97, preferably 40 to 89, particularly preferably 45 to 80.5, parts by mass of at least one N-alkylaziridine block copolymer having molar masses in the range from 500 to 50 000 g/mol and aziridino equivalent masses in the range from 250 to 25 000 g/equivalent;
(B) 1 to 10, preferably 1 to 5, particularly preferably 1.5 to 3, parts by mass of initiator substances which are suitable for curing the N-alkylaziridine block copolymers,
(C) 1 to 35, preferably 5 to 25, particularly preferably 8 to 20, parts by mass of organic diluents,
(D) 1 to 50, preferably 5 to 40, particularly preferably 10 to 30, parts by mass of modifiers, including fillers, dyes, pigments, thixotropic agents, flow improvers, polymeric thickeners, surface-active substances, fragrances and flavors.

The preparation produced by homogeneous mixing of the catalyst components and of the base components has, for example, a processing time at room temperature of between 0.5 and 10 minutes, and the preparation thus produced cures, for example, at a temperature range from 23 to 36° C. within a time span of from one to 20 minutes to give an elastically deformable material having a Shore A hardness of at least 20.

In the case of 2-component materials, the constituents (A) to (D) are divided into the base component and the catalyst component prior to mixing, so that the constituent (A) is present completely in the base component and the constituent (B) is present completely in the catalyst component. The constituents (C) and (D) may be present proportionately in the components.

The mixing ratio can be adjusted within a wide range via the composition of the two components, mixing ratios of catalyst component to base component of 1:1 to 1:5 having proven particularly practicable.

The proportions of the individual constituents (A) to (D) should be adjusted within the stated limits so that advantageous processibility with respect to mixing ratio and flow behavior is ensured and the criteria for the desired processing time, curing time and the mechanical properties of the cured material are fulfilled.

Constituent (A) contains the N-alkylaziridine block copolymers according to the invention. The use of mixtures of N-alkylaziridine block copolymers having different molar masses and aziridino equivalent masses is possible and is used for adjusting the properties of the materials.

To establish the desired mechanical properties of the cured materials, the preparations according to the invention may contain compounds having a polyether structure without silicone blocks and with at least one N-alkylaziridino group and preferably two N-alkylaziridino groups.

These additionally usable N-alkylaziridinopolyethers may have aziridino equivalent masses of 250 to 10 000 g/equivalent, it being possible for the polyether parent structures to be homopolymers of ethylene oxide, propylene oxide or tetrahydrofuran, random co- and terpolymers of said monomers and/or block copolymers of ethylene oxide and propylene oxide.

A number of compounds are suitable as an initiator substance according to constituents (B) of the mixed preparation, if they fulfill the criteria with respect to hardening rate and the resulting elastomeric properties.

Thus, those initiator substances which permit curing of the mixed preparation in a period of 1 to 20 minutes to give an elastic solid are suitable for use in two-component impression materials which are based on the polyether derivatives described above, these solids meeting the requirements for an elastic impression material according to DIN/EN 2482 and having a Shore A hardness (DIN 53505) of at least 20 after a storage time of 24 hours.

Many of the known initiators may be used as the initiator of the catalyst component. Those initiators or initiator systems which permit simple adjustment of the course of curing, produce no side effects and make it possible to achieve the required level of the mechanical properties in a reproducible manner are expediently used.

DE-C-914 325 proposes the use of oxonium, ammonium and sulfonium salts as initiator substances.

A summary of the initiator substances used for curing N-alkylaziridino compounds is contained in O. C.

DERMER, G. E. HAM, "Ethyleneimine and other Aziridines", Academic Press (1969).

Polymerization initiators which have proven to be suitable in principle are accordingly a large number of compound classes and compounds. When the cationic polymerization of aziridinopolyethers is used in practice, however, it is very difficult to establish the desired course of hardening with a sufficiently long processing time and rapid final curing. This object can be achieved by using special trisalkylsulfonium salts, as described, for example, in EP-A-0 110 429.

With the use of special trisalkylsulfonium salts, the criteria of the curing rate and of the properties of the elastic solid can in principle be achieved.

Patent Application DE-100 18 918 describes initiators which impart only a small degree of acidity to the catalyst component and which permit a readily adjustable, relatively long processing time after mixing of base component and catalyst component.

Initiator systems of this type are suitable for curing the base pastes according to the invention at the necessary rate. As a result of their use, the desired properties of the elastic solid can be achieved.

Patent Application DE-19942459 describes elastomer materials having an improved catalyst component which are distinguished by increased extendability. According to this invention, boric acid complexes are used as initiators. These initiators have proven particularly useful for curing N-alkylaziridinopolyethers according to the present invention and have advantages over other initiator systems when used.

Polyetherpolyols, such as polypropylene glycols or copolyetherols having tetrahydrofuran and/or ethylene oxide and/or propylene oxide units, polyesterpolyols, such as polycaprolactonediols and polycaprolactonetriols, polycarbonatediols, aliphatic esters, oils, fats, waxes, aliphatic hydrocarbons, araliphatic hydrocarbons and monofunctional or polyfunctional esters of polybasic acids, such as phthalic acid or citric acid, or esters or amides of alkanesulfonic acids and arylsulfonic acids are used as the organic diluent corresponding to constituent (C).

Furthermore, liquid organosiloxanes, such as polydimethylsiloxanes of different chain lengths, may be used.

Further compounds to be used according to this constituent comply with the following general structures:

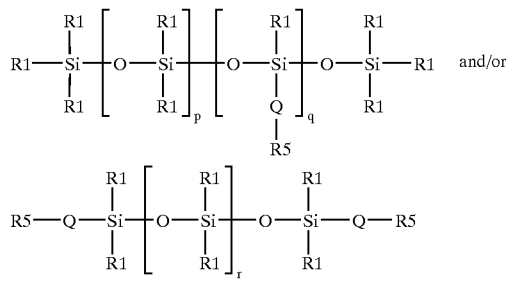

in which:

Q denotes an α,ω-polyether chain of the formula (3):

R5 denotes OH, OR1, O—C(O)—R1 or O—C(O)—NHR1;

g denotes 2 to 20, preferably 2 to 10, particularly preferably 2 to 7;

h denotes 1 to 1 000, preferably 1 to 500, particularly preferably 1 to 200;

a denotes 0 or 1;

f denotes an integer from 0 to 1 000, preferably 1 to 100, particularly preferably 1 to 50;

n denotes an integer from 1 to 10, preferably 1 to 5, particularly preferably 1 to 3;

p denotes an integer from 1 to 1 000, preferably 3 to 500;

q denotes an integer from 1 to 50, preferably 3 to 10;

r denotes an integer from 1 to 1 000, preferably 1 to 500.

Depending on the preparation process, the polydispersity of the polyether blocks may be 1.1 to 20 and preferably 2 to 10.

The polyether block may be a homopolymer, a copolymer or a terpolymer. The copolymers may have an alternating or random structure or may have alternating and random copolyether blocks which are optionally linked to homopolymeric polyether blocks.

Preferred polyether blocks are polytetrahydrofuran, polypropylene oxide, random copolymers of ethylene oxide and tetrahydrofuran, of propylene oxide and tetrahydrofuran or of ethylene oxide and propylene oxide, block copolymers of ethylene oxide and propylene oxide and random terpolymers of ethylene oxide, propylene oxide and tetrahydrofuran.

Modifiers corresponding to the constituent (D) may be added in a wide concentration range to the catalyst component as well as the base component.

These modifiers are generally finely divided fillers, such as aluminosilicates, precipitated silicas, quartz powder, wollastonite, mica powder and kieselguhr, and dyes and pigments, the addition of which permits a better assessment of the quality of mixing and reduces the danger of confusion, thixotropic agents, such as colloidal silicas and other additives influencing the flow behavior, such as polymeric thickeners, and furthermore surface-active substances for adjusting the flow behavior and fragrances and flavors.

Depending on the composition of the catalyst component and of the base component, the preparations according to the invention can be used for the adhesive bonding of substrates, and for sealing, coating and casting.

The materials according to the invention are particularly suitable as dental impression materials, bite-recording materials, modeling materials, temporary sealing materials, materials for the production of temporary crowns and bridges, and duplication materials.

The two components can be metered by visual inspection, such as by comparison of strand length, by weight, via prefilled pack units and subsequent manual mixing, from double-chamber cartridges with a static mixing tube or by means of volume metering systems with a downstream static or dynamic mixer.

In order to obtain optimum results, a high quality of mixing is required. On the other hand, the tolerance of the mixing ratio is generally relatively large and, for example in the case of a predetermined ratio of catalyst component to base component of 1:5, may comprise the range 0.8 to 1.2:5, without property changes which restrict the use being detectable.

The invention also relates to containers and mixing apparatuses containing the materials prepared from the preparations according to the invention, in particular dental materials, such as cartridges, bags, impression trays, static and dynamic mixers or mixing apparatuses.

The invention is explained in more detail by the following examples without it being restricted by these.

EXAMPLES

Synthesis Example 1

Preparation of Polyether-silicone-polyether Block Copolymers from an H-Terminated Silicone Oil and a Polyethylene Glycol Monoallyl Ether

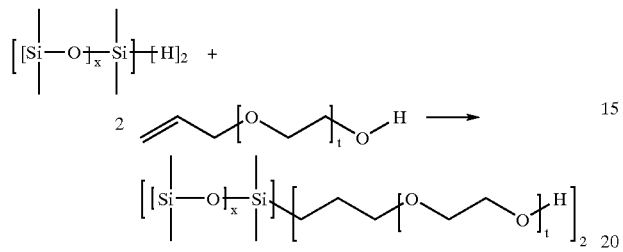

50 ml of toluene, 5 mg of hexachloroplatinic acid in isopropanol and 15 g of polyethylene glycol monoallyl ether (Clariant) [M=450; 0.034 mol] are added to 100 g of a silicone oil DMS-H21 (Gelest) [M=6 000; 0.017 mol]. The mixture is heated to 50° C., and the temperature is increased to 70° C. after a few hours and kept at 70° C. until checking of the conversion by means of IR spectroscopy indicates the disappearance of the C=C double bond. After customary working-up and product isolation, 110 g of a clear, colorless three-block polymer having an OH number of 16.3 remain.

Synthesis Example 2

Preparation of an Acrylate-terminated Polyether-silicone-polyether Block Copolymer from the Corresponding Block Copolymer Diol

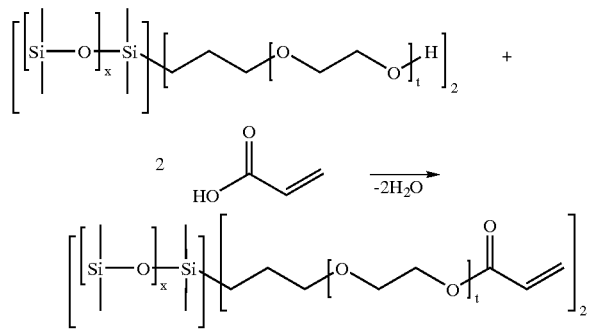

100 g of a silicone oil from synthesis example 1 [OH number=16.3; M=6 900; 0.0145 mol] are stabilized, and 200 ml of cyclohexane and 4.18 g of acrylic acid [M=72.06; 0.058 mol] are added to it. The reaction mixture is refluxed until no further water separates off and the reflux which condenses is as clear as water. After customary working-up and product isolation, 98 g of a clear, colorless acrylate block copolymer remain.

Synthesis Example 3

Preparation of an Aziridino Block Copolymer from an Acrylate-Terminated Polyether-silicone-polyether Block Copolymer

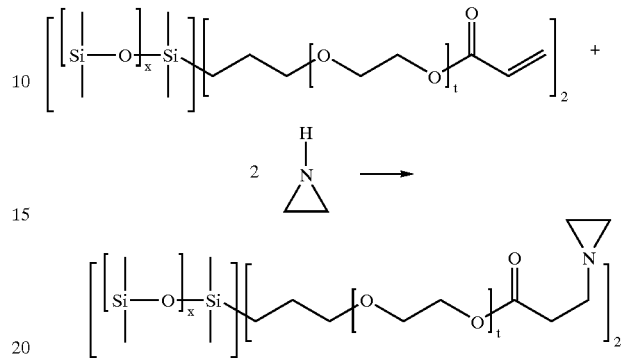

50 ml of toluene are added to 100 g of silicone oil from synthesis example 2 [M=7 000; 0.0143 mol]. At 30° C., 1.3 g of aziridine [M=43.07; 0.029 mol] are added dropwise. The mixture is heated to 50° C., and the temperature is increased to 100° C. after five hours and kept at 100° C. until checking of the conversion by means of IR spectroscopy indicates the disappearance of the double bond. After customary working-up and product isolation, 100 g of a clear, colorless aziridinosilicone remain.

Synthesis Example 4

Preparation of a Polyether-silicone-polyether Block Copolymer from an H-Terminated Silicone Oil and a Polyethylene Glycol Monoallyl Ether

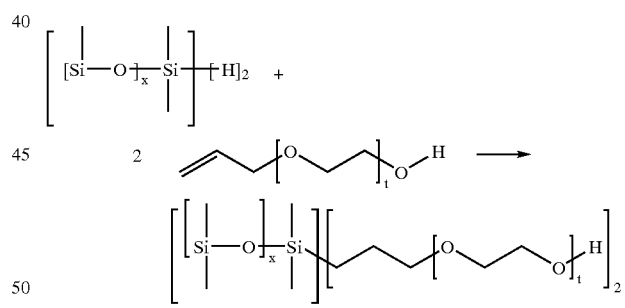

50 ml of toluene, 5 mg of hexachloroplatinic acid in isopropanol and 5.6 g of polyethylene glycol monoallyl ether (Clariant) [M=350; 0.016 mol] are added to 100 g of a silicone oil modifier 705 (Hanse Chemie) [M=12 500; 0.08 mol]. The mixture is heated to 50° C., and the temperature is increased to 70° C. after five hours and kept at 70° C. until checking of the conversion by means of IR spectroscopy indicates the disappearance of the double bond. After customary working-up and product isolation, 102 g of a clear, colorless three-block polymer having an OH number of 8.5 remain.

The conversion to the aziridine derivative was carried out according to example 13 of U.S. Pat. No. 3,453,242.

Synthesis Example 5

Preparation of a Polyether-silicone-polyether Block Copolymer from an H-terminated Silicone Oil and a Poly(Ethylene Glycol-co-propylene glycol) Monoallyl Ether

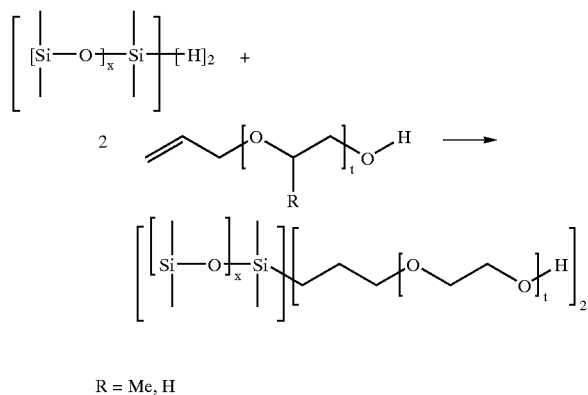

R = Me, H 50 ml of toluene, 5 mg of hexachloroplatinic acid in isopropanol and 68 g of Unisafe PKA-5013 (NOF) [M=2 000; 0.034 mol] are added to 100 g of a silicone oil DMS-H21 (Gelest) [M=6 000; 0.017 mol]. The mixture is heated to 50° C., and the temperature is increased to 70° C. after five hours and kept at 70° C. until checking of the conversion by means of IR spectroscopy indicates the disappearance of the double bond. After customary working-up and product isolation, 165 g of a slightly hazy, colorless three-block polymer having an OH number of 11.2 remain.

The conversion to the aziridine derivative was carried out according to example 13 of U.S. Pat. No. 3,453,242.

Synthesis Example 6

Preparation of a Polyether-silicone-polyether Block Copolymer from an H-terminated Silicone Oil and a Poly(Ethylene Glycol-co-Tetramethylene glycol) Monoallyl Ether

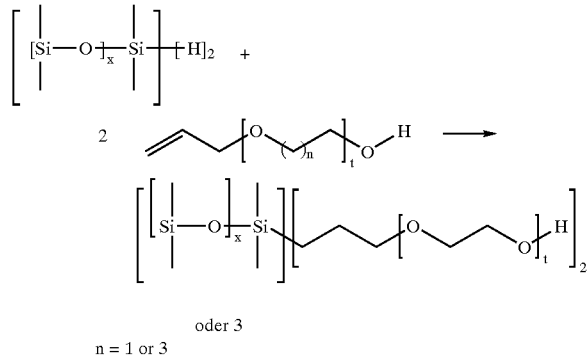

oder 3
n = 1 or 3

50 ml of toluene, 5 mg of hexachloroplatinic acid in isopropanol and 81.6 g of Unisafe PKA-7302 (NOF) [M=2 400; 0.034 mol] are added to 100 g of a silicone oil DMS-H21 (Gelest) [M=6 000; 0.017 mol]. The mixture is heated to 50° C., and the temperature is increased to 70° C. after five hours and kept at 70° C. until checking of the conversion by means of IR spectroscopy indicates the disappearance of the double bond. After customary working-up and product isolation, 178 g of a slightly hazy, colorless three-block polymer having an OH number of 10.4 remain.

The conversion to the aziridine derivative was carried out according to example 13 of U.S. Pat. No. 3,453,242.

Preparation Examples for Dental Materials

The catalyst components described below were prepared on a 100 g scale. The preparation of the base components which are described in table 1 was carried out on a 500 g scale.

Use Examples

Preparation of the Catalyst Components

Use Example 1 (K1)

44 g of acetyl tributyl citrate according to constituent (C) were initially introduced into a laboratory kneader and 20 g of β-(S-lauryl-S-ethylsulfonium) butyronitrile fluoroborate according to constituent (B) (cf. U.S. Pat. No. 4,167,618) were dissolved therein. 12 g of kieselguhr and 24 g of pyrogenic silica (HDK H 2000, from Wacker), both according to constituent (D), were incorporated into this mixture.

Use Example 2 (K2)

61.1 g of a poly(ethylene, propylene) glycol according to constituent (C) having a molar mass of 3 400 g/mol were initially introduced into a laboratory kneader, and 21 g of a hydrophobic precipitated silica according to constituent (D) (Sipernat D17, from Degussa) were added stepwise.

9.9 g of p-toluenesulfonic acid monohydrate according to constituent (B) were dissolved in 5 g of distilled water and added to the pasty mixture. After homogenization, a paste consisting of 2 g of zinc oxide according to constituent (B) and 1 g of poly(ethylene, propylene) glycol according to constituent (C) having a molar mass of 3 400 g/mol was added. The paste was kneaded for a further hour after the last addition.

Use Example 3 (K3)

In a laboratory kneader, 19 g of hydrophobic precipitated silica according to constituent (D) (Sipernat D17, from Degussa) were incorporated into 31 g of polypropylene oxide diol according to constituent (C) having a molar mass of 2 000 g/mol. The solution of a complex compound according to constituent (B), prepared from 3.6 g of boric acid and 17 g of salicyl alcohol, in 29.4 g of polypropylene oxide diol according to constituent (C) was added to the pasty mixture and the paste was kneaded for one hour.

Table 2 lists the mixtures which were investigated with the use of the catalyst components described and the base components described in table 1, in the weight ratio stated in each case.

The stated mixtures were prepared by application to a mixing block with a spatula in the course of 30 seconds and were used for determining the properties listed in table 2.

TABLE 1

Composition of the base component

| Compound | according to constituent | B1 | B2 | B3 | B4 | B5 | B6 |
|---|---|---|---|---|---|---|---|
| | | % by weight | | | | | |
| N-Alkyl-aziridino block copolymer according to synthesis example 3 | (A) | 59.3 | — | — | — | — | 8.3 |
| N-Alkyl-aziridine block copolymer according to synthesis example 4 | (A) | — | 63.2 | — | — | 50.1 | 55.1 |
| N-Alkyl-aziridine block copolymer according to synthesis example 5 | (A) | — | — | — | 57.6 | — | — |
| N-Alkyl-aziridine block copolymer according to synthesis example 6 | (A) | — | — | 54.3 | — | 9.8 | — |
| Dimethyl-siloxane AK 50 having a viscosity of 50 mPas | (C) | 10.1 | 4.1 | — | — | 4.9 | 10.0 |
| Dimethyl-siloxane AK 5000 having a viscosity of 5 000 mPas | (C) | 6.3 | 5.7 | — | — | 9.2 | 2.8 |
| Quartz powder (Silbond 600, Frechen) | (D) TST | — | — | 25.7 | 34.8 | 24.8 | — |
| Kieselguhr | (D) | 24.3 | 27.0 | 10.0 | — | — | 23.0 |
| Silicone-polyether block copolymer (Silwet L 7280, from Witco) | (C) | — | — | 1.8 | 2.6 | 1.2 | 0.8 |
| Dibenzyl-toluene | (C) | — | — | 2.0 | 5.0 | — | — |
| Mixture of bisaziridino-polyethers having an average imino equivalent mass of 3 100, prepared from a polyether-diol which consists of ethylene oxide and tetrahydrofuran units in the molar ratio of 1:3.5, having a content of 0.27% of cyclic polyethers | — | — | — | — | 6.2 | — | — |

The base components according to the invention and according to table 1 were distinguished by a very good shelf life.

+Thus, the samples stored at 36° C. over a period of 9 months could still be processed satisfactorily with the stated catalyst components and gave mechanical characteristics of the elastomer solid which deviated by less than 15% from the values which were measured at the beginning of storage.

TABLE 2

Materials according to the invention with the use of the catalyst component 1 to 3 and of base components according to table 1, and properties determined

| | Use examples No. | | | | | | | | |
|---|---|---|---|---|---|---|---|---|---|
| | 1 | 2 | 3 | 4 | 5 | 6 | 7 | 8 | 9 |
| Catalyst component (K) | K1 | K2 | K1 | K2 | K2 | K2 | K1 | K2 | K3 |
| Base component (B) | B1 | B2 | B3 | B4 | B5 | B6 | B2 | B3 | B3 |
| Mixing ratio (by weight) K:B | 1:4.5 | 1:5.0 | 1:5.1 | 1:5.0 | 1:4.7 | 1:5.0 | 1:4.5 | 1:5.0 | 1:4.3 |
| Processing time at 23° C.[a] [minutes] | 2.3 | 2.7 | 1.3 | 3.0 | 1.7 | 1.5 | 2.0 | 1.9 | 1.4 |
| End of curing at 23° C.[b] [minutes] | 7.2 | 8.3 | 4.9 | 8.1 | 4.7 | 4.2 | 6.9 | 5.7 | 7.9 |
| Elongation at break [%][a] | 71 | 87 | 102 | 81 | 58 | 99 | 79 | 91 | 125 |
| Tensile strength [MPa][a] | 0.81 | 0.79 | 0.94 | 1.01 | 0.74 | 1.07 | 0.99 | 0.95 | 0.98 |
| Shore A hardness after 24 h according to DIN 53505 | 44 | 45 | 49 | 47 | 39 | 36 | 35 | 38 | 33 |

[a] according to DIN/EN 4823
[b] The end of curing is defined as the time when an elastic solid which has no surface tack is present All mixtures of use examples 1 to 9 according to the invention (table 2) met the requirements for an elastic impression material and led to moldings which had a Shore A hardness (cf. table 2) substantially above 20 after a storage time of 24 hours at room temperature.

What is claimed is:

1. An N-alkylaziridine block copolymer of a formula (I):

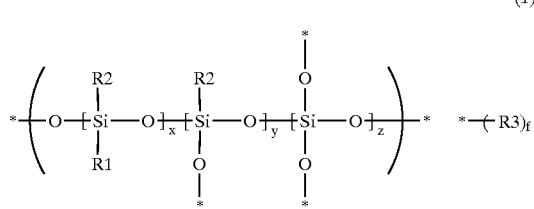

wherein
- R1 denotes a R1 radical selected from the group consisting of H, $C_1$–$C_{12}$-alkyl, $C_2$–$C_{12}$-alkenyl, $C_2$–$C_{12}$-alkynyl, $C_7$–$C_{15}$-alkaryl, $C_7$–$C_{15}$-aralkyl, and $C_3$–$C_{12}$-cycloalkyl, said R1 radical may be partly or completely substituted by Cl, F, or a mixture of Cl and F and said R1 radical may contain 0 to 5 hetero atoms selected from the group consisting of O, N and S;
- R2 denotes a R2 radical selected from the group consisting of R1 and R4;
- R3 denotes $SiR1_3$ or $SiR1_2R4$;
- R4 is a representative of the general formula (II):

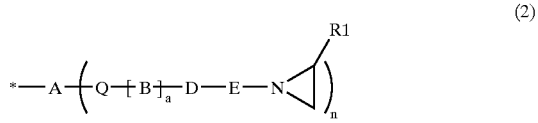

wherein
- A=(N+1)-valent saturated, unsaturated or aromatic, linear, branched or cyclic hydrocarbon radical comprising 1 to 18 carbon atoms and which may contain 0 to 5 hetero atoms selected from the group consisting of O, N and S;
- B=a representative selected from the group consisting of O, S, and NR1;
- D=a representative selected from the group consisting of C(O)O, C(O)NR1, C(O), C(S)NR1 and $CH_2$;
- E=a divalent saturated or unsaturated, linear, branched, or cyclic hydrocarbon radical which comprises 0 to 18 carbon atoms and which may contain 0 to 5 hetero atoms selected from the group consisting of O, N and S;
- Q=an α, ω-polyether chain of the general formula (III):

wherein
- g denotes 2 to 20;
- h denotes 1 to 1,000;
- a denotes 0 or 1;
- f denotes and integer from 2 to 1,000;
- n denotes an integer from 1 to 10;
- x, y and z each represent either 0 or integers whose sum is between 1 and 10,000 and
- if x is greater than 0, y or z is less than or equal to x.

2. A N-alkylaziridine block copolymer according to claim 1, wherein the N-alkylaziridine block copolymer contains at least two and up to 10 N-alkylaziridino groups per molecule.

3. A curable material based on N-alkylaziridine block copolymers according to claim 1, wherein, after mixing the components and based on 100 parts by mass, the curable material comprises:
- 30 to 97 parts by mass of at least one N-alkylaziridine block copolymer having a molar mass in the range from 500 to 50,000 g/mol and an aziridino equivalent mass in the range from 250 to 25,000 g/equivalent;
- 1 to 10 parts by mass of initiator substances for curing the N-alkylaziridine block copolymers;
- 1 to 35 parts by mass of organic dilutents; and
- 1 to 50 parts by mass of modifiers.

4. A curable material based on N-alkylaziridine block copolymers according to claim 2, wherein, after mixing the components and based on 100 parts by mass, the curable material comprises:
- 30 to 97 parts by mass of at least one N-alkylaziridine block copolymer having a molar mass in the range from 500 to 50,000 g/mol and an aziridino equivalent mass in the range from 250 to 25,000 g/equivalent;
- 1 to 10 parts by mass of initiator substances for curing the N-alkylaziridine block copolymers;
- 1 to 35 parts by mass of organic dilutents; and
- 1 to 50 parts by mass of modifiers.

5. A two-component dental material containing N-alkylaziridine block copolymers according to claim 1, comprising:
- a base component; and
- a catalyst component,
- wherein a preparation produced by homogeneous mixing of the catalyst component and the base component has a processing time of between 0.5 and 10 minutes at room temperature, and
- the preparation cures in a temperature range from 23 to 36° C. within a time span of one to 20 minutes to an elastically deformable material having a Shore A hardness of at least 20.

6. A two-component dental material containing N-alkylaziridine block copolymers according to claim 2, comprising:
- a base component; and
- a catalyst component,
- wherein a preparation produced by homogeneous mixing of the catalyst component and the base component has a processing time of between 0.5 and 10 minutes at room temperature, and
- the preparation cures in a temperature range from 23 to 36° C. within a time span of one to 20 minutes to an elastically deformable material having a Shore A hardness of at least 20.

7. A method of using an N-alkylaziridine block copolymer according to claim 1, comprising preparing curable materials.

8. A method of using an N-alkylaziridine block copolymer according to claim 2, comprising preparing curable materials.

9. A method of using an N-alkylaziridine block copolymer according to claim 1, comprising preparing dental materials.

10. A method of using an N-alkylazirdine block copolymer according to claim 2, comprising preparing dental materials.

11. A method of using a curable material according to claim 3, comprising adhesive bonding, coating, or casting substrates in the dental sector.

12. A method of using a curable material according to claim 11, wherein the use is for dental impression materials, bite-recording materials, modeling materials, temporary sealing materials, materials for the production of temporary crowns and bridges, or duplication materials.

13. A method of using a two-component dental material according to claim 5, comprising adhesive bonding, coating, or casting substrates in the dental sector.

14. A method of using a two-component dental material according to claim 13, wherein the use is for dental impression materials, bite-recording materials, modeling materials, temporary sealing materials, materials for the production of temporary crowns and bridges, or duplication materials.

15. A container comprising at least one material according to claim 3.

16. A container comprising at least one material according to claim 4.

17. A container comprising at least one material according to claim 5.

18. A container comprising at least one material according to claim 6.

* * * * *

UNITED STATES PATENT AND TRADEMARK OFFICE
CERTIFICATE OF CORRECTION

PATENT NO.       : 6,867,246 B2
APPLICATION NO.  : 10/296996
DATED            : March 15, 2005
INVENTOR(S)      : Reinhold Nowak Page 1 of 1

It is certified that error appears in the above-identified patent and that said Letters Patent is hereby corrected as shown below:

<u>On the Title Page, in Column 2, item [57] under (Abstract)</u>
Line 3, after "$C_7 - C_{15}$" delete "aralkyl" and insert -- alkaryl --, therefor.

<u>Column 17</u>
In Column 1, in Row 8, under (TABLE 1), line 35, after "Silbond" insert -- TST --.
In Column 2, in Row 8, under (TABLE 1), line 35, below "(D)" delete "TST".

<u>Column 19</u>
Line 39, in Claim 1, delete "(N+1)" and insert -- (n+1) --, therefor.
Line 60, in Claim 1, delete "and" and insert -- an --, therefor.
Line 63, in Claim 1, after "10,000" insert -- , --.

<u>Column 20</u>
Line 12, in Claim 3, delete "dilutents" and insert -- diluents --, therefor.
Line 62, in Claim 10, delete "N-alkylazirdine" and insert -- N-alkylaziridine --, therefor.

Signed and Sealed this

Thirteenth Day of May, 2008

JON W. DUDAS
*Director of the United States Patent and Trademark Office*